United States Patent [19]

Weber, Jr.

[11] 4,123,450

[45] Oct. 31, 1978

[54] PROCESS FOR PREPARING ALKYL ISOCYANATES

[75] Inventor: Harry W. Weber, Jr., Newtown, Pa.

[73] Assignee: FMC Corporation, Philadelphia, Pa.

[21] Appl. No.: 835,564

[22] Filed: Sep. 22, 1977

[51] Int. Cl.$^2$ .......................................... C07C 118/00
[52] U.S. Cl. ............................... 260/453 P; 260/463; 560/132
[58] Field of Search ..................... 260/453 P; 560/132

[56] References Cited

U.S. PATENT DOCUMENTS

| 2,409,712 | 10/1946 | Schweitzer | 260/453 P |
| 3,076,007 | 1/1963 | Barclay, Jr. et al. | 260/453 P |
| 3,202,573 | 8/1965 | Haubein | 424/300 |
| 3,734,941 | 5/1973 | Sydor | 260/453 P |
| 3,919,279 | 11/1975 | Rosenthal et al. | 260/453 P |
| 4,003,938 | 1/1977 | Koenig et al. | 260/453 P |

FOREIGN PATENT DOCUMENTS 1,200,768  8/1970  United Kingdom.

OTHER PUBLICATIONS

Strain et al., JACS, vol. 72, p. 1254 (1950).
Crosby et al., JACS, vol. 76, p. 4458 (1954).
Kirk-Othmer Encyclopedia of Chemical Technology, 2nd Ed., vol. 12, p. 54, Interscience, 1967.
Jacobi et al., Chemical Abstracts, vol. 53, 22718d (1959).

Primary Examiner—Dolph H. Torrence
Attorney, Agent, or Firm—Robert L. Andersen; H. Robinson Ertelt

[57] ABSTRACT

Alkylisocyanates are prepared by reacting a phenol or substituted phenol and phosgene in a halogenated hydrocarbon solvent with aqueous alkali metal hydroxide to produce a corresponding chloroformate, reacting the resulting chloroformate solution with aqueous alkylamine to give a corresponding N-alkylcarbamate which, after solvent is stripped, is then pyrolyzed to yield the alkyl isocyanate. Solvent and the starting phenol may be recovered and recycled to the process.

7 Claims, No Drawings

PROCESS FOR PREPARING ALKYL ISOCYANATES

The present invention relates to a process for preparing alkyl isocyanates, particularly lower alkyl isocyanates such as methyl isocyanate, by reacting a suitable phenol, phosgene and an alkylamine to produce a corresponding phenyl N-alkylcarbamate and then pyrolyzing the phenyl N-alkylcarbamate. The two reaction steps to synthesize the carbamate each utilize a phase transfer system in which a halogenated hydrocarbon serves as solvent for the organic components and aqueous alkali metal hydroxide serves as acid acceptor and solvent for water soluble by-products. After each reaction step the aqueous phase is separated and discarded. The halogenated hydrocarbon and the unreacted phenol are separately recovered and may be recycled in the process.

In the first step a phenol of the formula

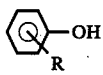

wherein R is alkyl having one or two carbon atoms or hydrogen, (hereinafter referred to generically as a "hydroxybenzene" except where phenol per se is intended) and phosgene in a solvent amount of a halogenated hydrocarbon are reacted with aqueous alkali metal hydroxide to produce a two-phase reaction mixture comprising an organic phase of the corresponding phenyl chloroformate and an aqueous by-product phase. The reaction proceeds in accordance with the equation:

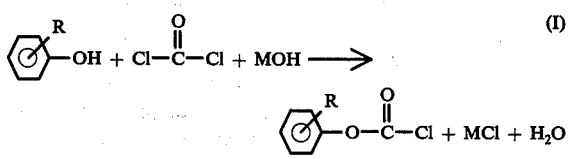

The reaction is conducted by dissolving the hydroxybenzene and phosgene in a suitable halogenated hydrocarbon solvent to form the organic component and adding aqueous alkali metal hydroxide.

The ratio of phosgene to the hydroxybenzene in the organic component may vary over a fairly broad range. For example about 0.5 to about 1.5 moles of phosgene may be employed in the organic component for each mole of the hydroxybenzene. For more economical operation it is advantageous to utilize approximately equimolar amounts or a small excess or deficiency of phosgene, for example from about 0.9 to about 1.2 moles of phosgene per mole of the hydroxybenzene.

Suitable halogenated hydrocarbon solvents include those in which the hydrocarbon moiety has one to four carbon atoms, advantageously one or two carbon atoms, preferably one carbon atom. The preferred hydrocarbons are alkanes. The hydrocarbon is substituted with one or more halogen substituents which may be independently selected from chlorine, bromine or fluorine. A typical example is methylene chloride.

Aqueous alkali metal hydroxide is then added slowly to the organic component with vigorous agitation. Preferably the aqueous alkali metal hydroxide is added dropwise to a well agitated solution of phenol and phosgene in methylene chloride. The temperature of the reaction mixture during the reaction is suitably below about 50° C, advantageously below about 35° C, but above the temperature at which ice forms. The aqueous alkali metal hydroxide may suitably be employed at a concentration in the range of about 10 percent by weight up to about 25% by weight. Sufficient aqueous alkali metal hydroxide should be utilized to provide a reaction mixture in which the post-addition pH of the aqueous phase is about 7. Sufficient water should be present to dissolve salts formed during the reaction.

After addition of aqueous alkali metal hydroxide, agitation is stopped, the phases are allowed to separate and the aqueous phase is removed and discarded. The organic phase comprising a solution of the corresponding chloroformate in the organic solvent is utilized in the next step. The aqueous phase is preferably separated from the organic phase prior to further processing in order to minimize losses due to formation of a corresponding phenyl carbonate in the next reaction step.

The use of more than about a 20% molar excess of phosgene in the starting organic component increases the conversion of the hydroxybenzene to the corresponding chloroformate. However, the use of a larger excess of phosgene is impractical because it results in excessive losses of phosgene or necessitates the use of a separate phosgene recovery step.

In the second step the organic phase recovered from step 1 is reacted with aqueous alkylamine and aqueous alkali metal hydroxide to form the corresponding phenyl N-alkylcarbamate in accordance with the equation:

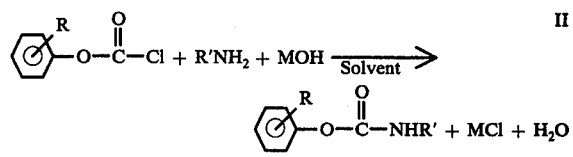

wherein R is as defined above and R' is alkyl, preferably having 1 to 4 carbon atoms. The R' alkyl corresponds to the alkyl moiety of the alkyl isocyanate formed upon pyrolysis. No separation or purification of the chloroformate from or in the organic phase is required prior to performance of this step 2.

Step 2 is suitably conducted at any temperature between the freezing and boiling points of the reaction mixture. The organic phase from step 1 is mixed with aqueous alkali metal hydroxide with agitation. Several methods of addition are contemplated by the present invention. For example, aqueous alkylamine may be added to the organic chloroformate phase from step 1, or vice versa, and this may be followed by addition of aqueous alkali metal hydroxide. Similarly, aqueous solutions of alkylamine and aqueous alkali metal hydroxide may be added separately or mixed together and added to the organic phase as a single aqueous solution. If the alkylamine and alkali metal hydroxide are simultaneously added it is important that the addition rate of the amine be equal to or greater than that of the alkali metal hydroxide on a molar basis, as the presence of excess alkali metal hydroxide will increase losses due to phenyl carbonate formation. In addition, agitation of the reaction mixture is required during addition of the alkali metal hydroxide. While the concentration of alkylamine and/or alkali metal hydroxide is not critical, sufficient water should be utilized to dissolve the water soluble salts formed during the reaction. A substantially equimolar amount of alkali metal hydroxide and alkylamine, based on the chloroformate present, is utilized in this step. Yields in this step are substantially quantitative based on chloroformate present in the organic phase. Unreacted hydroxybenzene and phenyl carbonate originally present remain essentially unchanged.

After the aqueous and organic phases are thoroughly mixed the reaction mixture is allowed to separate and the aqueous phase is removed and discarded. The organic phase comprising a solution of the corresponding N-alkylcarbamate and solvent is utilized in step 3.

In step 3, solvent is stripped at elevated temperature from the organic phase resulting from step 2. The solvent may be stripped by any convenient means. Preferably, stripping is conducted to a final temperature above the temperature at which the carbamate melts, but below the temperature at which alkyl isocyanate is released. The precise temperature will depend on the purity of the carbamate and the pressure employed. The solvent recovered is essentially free of the unreacted hydroxybenzene and may be recycled and utilized in step 1 above.

In step 4 the bottoms product of step 3 is pyrolyzed and alkyl isocyanate is selectively condensed by being taken overhead through a primary condenser maintained at a temperature above the condensation temperature of the alkyl isocyanate but below the condensation temperature of the hydroxybenzene. The hydroxybenzene is condensed and returned to the pyrolysis vessel or separately collected. The alkyl isocyanate passes through the primary condenser and is subsequently condensed and collected. For pyrolysis of phenyl N-methylcarbamate a 100° C primary condenser may be used to condense phenol. The methyl isocyanate passes through this condenser and may be condensed and collected at about 0°–10° C.

During pyrolysis a pot composition is reached at which further evolution of alkyl isocyanate effectively ceases. For pyrolysis of phenyl N-methylcarbamate this point is reached when the pot composition reaches a molar ratio of about 1 part carbamate to about 3 parts phenol. When this occurs the pot may be cooled, a vacuum applied and phenol stripped at reduced pressure and at a temperature below the temperature and pressure which will cause release of the alkyl isocyanate. For phenyl N-methylcarbamate a pressure of 20mm Hg is a practical pressure at which to remove sufficient phenol to permit recycle of the residual carbamate to the pyrolysis step. At approximately 20mm Hg stripping may be conducted to a temperature of about 130° C. Phenol stripped under such conditions is sufficiently pure to be recycled and reutilized in step 1. The carbamate pot bottoms, stripped of most of the phenol, may then be recycled to the pyrolyzer.

The alkyl isocyanate recovered may be utilized for any known use including use as an intermediate in the preparation of carbamates by reaction with a suitable alcohol, for example in the preparation of insecticidal carbamates commonly used as crop protection agents.

The examples which follow demonstrate the practice of the present invention.

EXAMPLE 1

Preparation of Phenyl Chloroformate

Condensed phosgene (103.8g, 1.05 mole) was added rapidly with stirring at ice bath temperature to a solution of phenol (94.1g, 1.00 mole) in methylene chloride (825 ml) in a high shear mixer equipped with turbine-type stirrer and Teflon baffles arranged in a cage structure. An aqueous solution of sodium hydroxide (48.0g, 1.20 mole, 20% by weight, 240g total solution) was added dropwise with vigorous stirring over a one-hour period giving a white emulsion. The reaction mixture was then transferred to a separatory funnel and the organic phase was separated. Analysis of the organic phase confirmed that 0.90 moles of phenol had been converted to phenyl chloroformate, about 0.03 moles of phenol had been converted to phenyl carbonate and about 0.07 moles phenol remained unreacted. No residual phosgene was detected. The pH of the discarded aqueous phase was 7.

EXAMPLE 2

Preparation of Phenyl N-methylcarbamate

A 40% by weight aqueous solution of methylamine (28.0g, 0.90 mole) and 20% by weight aqueous sodium hydroxide (36.0g, 0.90 mole) were added dropwise simultaneously over a 30 minute period to a stirred solution of the organic phase from Example 1, containing phenyl chloroformate 140.9g, 0.90 mole) in methylene chloride. The organic phase was separated and solvent was removed under reduced pressure to give a mixture of phenyl N-methylcarbamate (0.90 mole), phenol (0.07 mole) and diphenylcarbonate (0.015 mole).

EXAMPLE 3

Thermal Decomposition of Phenyl N-methylcarbamate

A sample of phenyl N-methylcarbamate was charged to a single-neck round-bottom flask connected to a steam condenser topped by a distillation head with a secondary condenser maintained at 0° to 10° C. The flask was heated gradually to 208° C. Methyl isocyanate evolution started at 190° C. As the vapor passed through the steam condenser phenol was condensed and returned to the flask. The methyl isocyanate vapor was condensed by the secondary condenser and collected. The methyl isocyanate assayed after derivatization appeared chromatographically pure.

Following pyrolysis the residual material in the flask had a composition of 25 mole percent phenyl N-methylcarbamate and 75 mole percent phenol. The flask was cooled, a vacuum applied and phenol was stripped at a pressure of 20 mm Hg. Recovered phenol was also chromatographically pure. The residual carbamate remaining after phenol was stripped was returned to the pyrolysis flask. After 3 cycles of pyrolysis and phenol stripping, analysis showed: 96% conversion to methyl isocyanate, 2% unconverted material and 2% conversion to the allophanate. The methyl isocyanate was identified by reaction with aniline to give 1-methyl-3-phenylurea melting at 149°–150.5° C.

EXAMPLE 4

Preparation of Phenyl N-ethylcarbamate

An aqueous solution of ethylamine (2.58g of 70% solution, 0.04 mole) and an aqueous sodium hydroxide solution (1.44g in 8 ml solution, 0.036 mole) were added dropwise simultaneously over a period of 15 minutes to a cool solution of phenyl chloroformate (6.0g, 0.038 mole) in methylene chloride (35 ml). The reaction mixture was stirred for one hour, then separated. The organic layer was dried over anhydrous magnesium sulfate, then filtered and stripped of solvent on a Rotovap. White crystals of phenyl N-ethylcarbamate weighing 6.27g were obtained having a melting point of 49°–50° C.

EXAMPLE 5

Thermal Decomposition of Phenyl N-ethylcarbamate

Phenyl N-ethylcarbamate (2.5g, 0.015 mole) was heated in a 15 ml flask with a short column and air-cooled condenser. At a sand bath temperature of 180° C distillate began to come over and the product was collected at a vapor temperature of 55°–58° C in a receiving flask cooled with dry ice and acetone. Ethyl isocyanate (0.91g) was obtained in 84% yield. Analysis by GC indicated that the product was 96.11% pure.

EXAMPLE 6

Preparation of Phenyl N-butyl-carbamate

Using the same procedure as in Example 4, n-butylamine (2.93g, 0.04 mole) was reacted with phenyl chloroformate (6.0g, 0.038 mole) in 35 ml methylene chloride and with aqueous sodium hydroxide. The reaction mixture was stirred for 2 hours, then allowed to separate. The pale yellow-green organic layer was dried over anhydrous magnesium sulfate and gravity filtered. The solvent was removed under reduced pressure, leaving white crystals weighing 7.13g (97% yield, MP 39°–40° C.). GC analysis indicated that the phenyl N-butylcarbamate was 93% pure.

EXAMPLE 7

Thermal Decomposition of Phenyl N-butylcarbamate

Phenyl N-butylcarbamate (2.5g, 0.013 mole) was heated in the manner described in Example 5. Butyl isocyanate (0.76g) was obtained at a vapor temperature of 65°–100° C and a sand bath temperature of 150°–220° C.

EXAMPLE 8

Preparation of Phenyl N-isopropylcarbamate

Using the same procedure as in Example 4, isopropylamine (2.36g, 0.04 mole) was reacted with phenyl chloroformate (6.0g, 0.038 mole) in methylene chloride (35 ml) and with aqueous sodium hydroxide. The reaction mixture was stirred for two hours, then allowed to separate. The organic layer was dried over anhydrous magnesium sulfate, then gravity filtered. The filtrate was stripped of solvent on the Rotovap, leaving pure white crystals weighing 6.66g, MP 81°–82° C.

EXAMPLE 9

Thermal Decomposition of Phenyl N-isopropylcarbamate

Thermal decomposition of phenyl N-isopropylcarbamate (2.5g, 0.014 mole) was carried out in the manner described in Example 5. Isopropyl isocyanate (0.84g, 71% yield) was collected at a vapor temperature of 50°–80° C. GC analysis of the isopropyl isocyanate indicated a purity of 94.6%.

I claim:
1. A process for producing an alkyl isocyanate which comprises:
   (1) reacting a hydroxybenzene of the formula

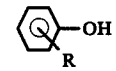

wherein R is hydrogen or lower alkyl of 1 or 2 carbon atoms, and phosgene in a halogenated hydrocarbon solvent with an aqueous alkali metal hydroxide, permitting the aqueous and organic phases to separate, removing the aqueous phase and recovering the organic phase comprising a solution of the corresponding chloroformate in said solvent,
   (2) reacting the organic phase recovered from step 1, in the presence of an alkali metal hydroxide, with an alkylamine in which the alkyl group corresponds to the alkyl group of the alkyl isocyanate, allowing the aqueous and organic phases to separate, and recovering the organic phase comprising a solution of the corresponding N-alkylcarbamate in said solvent,
   (3) stripping said solvent from the organic phase resulting from step (2),
   (4) pyrolyzing the bottoms product of step (3) and selectively condensing and collecting said alkyl isocyanate.

2. The process of claim 1 including the additional step of stripping said hydroxybenzene from the bottoms product of step 4 and recycling the resulting residual carbamate to step 4.

3. The process of claim 2 wherein solvent from step 3 and said hydroxybenzene are recycled to step (1).

4. The process of claim 1 wherein said alkyl isocyanate is a lower alkyl isocyanate in which the alkyl group has 1 to 4 carbon atoms.

5. The process of claim 4 wherein said alkyl isocyanate is methyl isocyanate.

6. The process of claim 1 wherein said hydroxybenzene is phenol.

7. The process of claim 1 wherein said halogenated hydrocarbon is methylene chloride.

* * * * *